United States Patent
Cavaco Paulo et al.

(10) Patent No.: US 9,393,320 B2
(45) Date of Patent: Jul. 19, 2016

(54) LIPOSOMES AND ITS PRODUCTION METHOD

(71) Applicants: Artur Manuel Cavaco Paulo, Guimarães (PT); Ana Arminda Lopes Preto de Almeida, Braga (PT); Eugénia Sofia Da Costa Nogueira, Pousa (PT); Andreia Ferreira Castro Gomes, Braga (PT)

(72) Inventors: Artur Manuel Cavaco Paulo, Guimarães (PT); Ana Arminda Lopes Preto de Almeida, Braga (PT); Eugénia Sofia Da Costa Nogueira, Pousa (PT); Andreia Ferreira Castro Gomes, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

(21) Appl. No.: 14/363,698

(22) PCT Filed: Dec. 7, 2012

(86) PCT No.: PCT/IB2012/057083
§ 371 (c)(1),
(2) Date: Jun. 6, 2014

(87) PCT Pub. No.: WO2013/084208
PCT Pub. Date: Jun. 13, 2013

(65) Prior Publication Data
US 2014/0335164 A1   Nov. 13, 2014

(30) Foreign Application Priority Data
Dec. 7, 2011 (PT) .......................... 106050

(51) Int. Cl.
  *A61K 38/16*  (2006.01)
  *C07K 16/08*  (2006.01)
  *A61K 47/48*  (2006.01)
  *C12N 15/113* (2010.01)
  *A61K 9/127*  (2006.01)

(52) U.S. Cl.
  CPC ..... *A61K 47/48815* (2013.01); *A61K 47/48107* (2013.01); *C12N 15/113* (2013.01); *A61K 9/1271* (2013.01)

(58) Field of Classification Search
  None
  See application file for complete search history.

(56) References Cited

U.S. PATENT DOCUMENTS

2003/0170299 A1   9/2003   Lee et al.

FOREIGN PATENT DOCUMENTS

| CA | 2 553 426 A1 | 8/2005 |
| WO | WO 2007/006041 A2 | 1/2007 |
| WO | WO 2007/139815 A2 | 12/2007 |

OTHER PUBLICATIONS

Turk et. al. Biochemica Physica Acta, 1559 (2002) 56-68.*
Zhao, P. et al. (2010). Paclitaxel-loaded, folic-acid-targeted and TAT-peptide-conjugated polymeric liposomes: In Vitro and In Vivo evaluation. *Pharmaceutical Resesarch*, 27(9), 1914-1926.
Vogel, K. et al. (1996). Peptide-mediated release of folate-targeted liposome contents from endosomal compartments. *Journal of the American Chemical Society*, 118(7), 1581-1586.
Turk, M. J. et al. (2002). Characterization of a novel pH-sensitive peptide that enhances drug release from folate-targeted liposomes at endosomal pHs. *Biochimica at Biophysica Acta*, 1559(1), 56-68.
Low, P. S. (2008). Discovery and development of folic-acid-based receptor targeting for imaging and therapy of cancer and inflammatory diseases. *Accounts of Chemical Research*, 41(1), 120-129.
Hilgenbrink, A. R. and Low, P. S. (2005). Folate receptor-mediated drug targeting: From therapeutics to diagnostics. *Journal of Pharmaceutical Sciences*, 94(10), 2135-2146.
International Search Report, mailed Sep. 9, 2013 in connection with PCT International Application No. PCT/IB2012/057083, filed Dec. 7, 2012.
Written Opinion of the International Searching Authority, mailed Sep. 9, 2013 in connection with PCT International Application No. PCT/IB2012/057083, filed Dec. 7, 2012.
Notification Concerning Transmittal of International Preliminary Report on Patentability (Chapter I of the Patent Cooperation Treaty), including an International Preliminary Report on Patentability and Written Opinion of the International Searching Authority, mailed Jun. 19, 2014 by The International Bureau of WIPO in connection with PCT International Application No. PCT/IB2012/057083, filed Dec. 7, 2012.

* cited by examiner

*Primary Examiner* — Jeanette Lieb
(74) *Attorney, Agent, or Firm* — John P. White; Cooper & Dunham LLP

(57) ABSTRACT

The present invention is the use of conjugated peptide sequences for inclusion in liposomal membranes. The combination can be done with folic acid or with an antibody of folic acid receptor coupled to N-terminal peptide. The presence of these peptides conjugated to liposomal formulations allows the targeting and subsequent release of therapeutic agents and/or imaging agents to cells expressing folic acid receptor.
The developed method combines the ability of liposomes in the transport and release of drugs and the specific expression of folic acid receptor on the surface of cell membranes that allow transmembrane transport mediated by specific liposomes. Thus allows the transport of therapeutic agents and/or imaging agents, which are inside the liposome, either hydrophobic or hydrophilic. The therapeutic agents can be either pharmacological compounds (active agents) or siRNAs (small interference RNA) specific to defined target genes.

20 Claims, No Drawings

SEQUENCE LISTING

<160> NUMBER OF SEQ ID NOS: 13

<210> SEQ ID NO 1
<211> LENGTH: 14
<212> TYPE: PRT
<213> ORGANISM: Homo sapiens

<400> SEQUENCE: 1

Lys Arg Phe Phe Pro Asp Thr Phe Gly Ile Lys Phe Leu Asp
1               5                   10

<210> SEQ ID NO 2
<211> LENGTH: 14
<212> TYPE: PRT
<213> ORGANISM: Homo sapiens

<400> SEQUENCE: 2

Lys Arg Leu Leu Pro Asp Thr Leu Gly Ile Lys Leu Leu Asp
1               5                   10

<210> SEQ ID NO 3
<211> LENGTH: 22
<212> TYPE: PRT
<213> ORGANISM: Homo sapiens

<400> SEQUENCE: 3

Ile Leu Leu Arg Lys Leu His Val Pro Phe Phe Pro Ile Gly Phe Arg
1               5                   10                  15

Gly Arg Pro Ala Ala Ser
            20

<210> SEQ ID NO 4
<211> LENGTH: 22
<212> TYPE: PRT
<213> ORGANISM: Homo sapiens

<400> SEQUENCE: 4

Ile Leu Leu Arg Lys Leu His Val Pro Ile Ile Pro Ile Gly Ile Arg
1               5                   10                  15

Gly Arg Pro Ala Ala Ser
            20

<210> SEQ ID NO 5
<211> LENGTH: 22
<212> TYPE: PRT
<213> ORGANISM: Homo sapiens

<400> SEQUENCE: 5

Ile Leu Leu Arg Lys Leu His Val Pro Trp Trp Pro Ile Gly Trp Arg

```
1               5                  10                 15

Gly Arg Pro Ala Ala Ser
            20

<210> SEQ ID NO 6
<211> LENGTH: 22
<212> TYPE: PRT
<213> ORGANISM: Homo sapiens

<400> SEQUENCE: 6

Ile Leu Leu Arg Lys Leu His Val Pro Tyr Tyr Pro Ile Gly Tyr Arg
1               5                  10                 15

Gly Arg Pro Ala Ala Ser
            20

<210> SEQ ID NO 7
<211> LENGTH: 22
<212> TYPE: PRT
<213> ORGANISM: Homo sapiens

<400> SEQUENCE: 7

Ile Leu Leu Arg Lys Leu His Val Ala His Gly Ala Ile Gly Ile Arg
1               5                  10                 15

Gly Arg Pro Ala Ala Ser
            20

<210> SEQ ID NO 8
<211> LENGTH: 22
<212> TYPE: PRT
<213> ORGANISM: Homo sapiens

<400> SEQUENCE: 8

Ile Leu Leu Arg Lys Leu His Val Cys His Gly Cys Ile Gly Ile Arg
1               5                  10                 15

Gly Arg Pro Ala Ala Ser
            20

<210> SEQ ID NO 9
<211> LENGTH: 11
<212> TYPE: PRT
<213> ORGANISM: Homo sapiens

<400> SEQUENCE: 9

Asp Arg Asp Asp Gln Gly Gln Val Gln His Leu
1               5                  10

<210> SEQ ID NO 10
<211> LENGTH: 11
<212> TYPE: PRT
<213> ORGANISM: Homo sapiens

<400> SEQUENCE: 10

Asp Arg Asp Asp Gln Ala Ala Phe Ser Gln Tyr
1               5                  10

<210> SEQ ID NO 11
<211> LENGTH: 20
<212> TYPE: PRT
<213> ORGANISM: Homo sapiens

<400> SEQUENCE: 11

Asp Arg Asp Asp Gly Ala Gly Ala Gly Ala Gly Ala Gly Ala Gly Ala
1               5                  10                 15
```

-continued

```
Gly Ala Gly Ala
         20

<210> SEQ ID NO 12
<211> LENGTH: 12
<212> TYPE: PRT
<213> ORGANISM: Homo sapiens

<400> SEQUENCE: 12

Asp Arg Asp Asp Val Gln His Leu Gln Ala Ala Phe
1               5                   10

<210> SEQ ID NO 13
<211> LENGTH: 12
<212> TYPE: PRT
<213> ORGANISM: Homo sapiens

<400> SEQUENCE: 13

Asp Arg Asp Asp Ile Leu Gln Thr Ala Gly Ala Leu
1               5                   10
```

LIPOSOMES AND ITS PRODUCTION METHOD

CROSS-REFERENCE TO RELATED APPLICATIONS

This application is a §371 national stage of PCT International Application No. PCT/IB2012/057083, filed Dec. 7, 2012, claiming priority of Portuguese Patent Application No. 106050, filed Dec. 7, 2011, the contents of each of which are hereby incorporated by reference in their entirety.

REFERENCE TO A SEQUENCE LISTING

This application incorporates-by-reference nucleotide and/or amino acid sequences which are present in the file named "140606_5126_86546_Substitute_Sequence_Listing_GC.txt," which is 3.20 kilobytes in size, and which was created Jun. 5, 2014 in the IBM-PC machine format, having an operating system compatibility with MS-Windows, which is contained in the text file filed Jun. 6, 2014 as part of this application.

FIELD OF THE INVENTION

The present invention relates to formulations of peptides and liposomes and the appropriate production method. More specifically refers to the inclusion of conjugated peptides in liposomal formulations. The conjugated peptides containing folic acid or antibody of the folic acid receptor at the N-terminal amino acid sequence, allowing the targeting of liposomes to cells with the folic acid receptor to the surface and specific release of pharmacological active principles or siRNAs within these same cells. This system can be used in the pharmaceutical field.

BACKGROUND OF THE INVENTION

Liposomes are vesicular systems composed of a lipid bilayer, used like cell models in basic research. Liposomes have gained extensive attention as carriers for a wide range of drugs due being both nontoxic and biodegradable because they are composed of naturally occurring substances existing in biological membranes. Biologically active materials encapsulated within liposomes are protected to varying extent from immediate dilution or degradation, which makes them good drug delivery systems for the transport of drugs or other bioactive compounds to organs affected. The unique ability of liposomes to entrap drugs both in an aqueous and a lipid phase make such delivery systems attractive for hydrophilic and hydrophobic drugs (Chrai S. et al., 2002; Hong M. et al., 2001). Liposome technology has broad potential applications, from cosmetics to delivery of drugs in cancer chemotherapy, anti-inflammatory therapy, cancer imaging agents and gene therapy. However, the delivery of therapeutical compounds is restricted by the low selectivity of therapeutic drugs, resulting in by harmful toxic effects on normal organs and tissues (Immordino M. et al., 2006). The delivery of the compounds to specific cell types, for example, cancer cells or cells of specific tissues and specific organs can be realized by using receptors associated with specific cell types. Unlike many other methods, receptor mediated endocytotic activity can be used successfully both in vivo and in vitro (Varghese B. et al., 2007). Receptor mediated endocytosis involves the movement of ligands bound to membrane receptors into the interior of an area bounded by the membrane through invagination of the membrane. Thus, for the purpose of selectively making a drug delivery to specific tissues and cells, the surface of the liposomes can often be modified with specific ligands (Gabizon. A. et al., 1999; Turk M. et al., 2002). Particular receptors are overexpressed in certain cancerous cells, including the high affinity folic acid receptor. The high affinity folate receptor is a tumour marker that is overexpressed in a variety of neoplastic tissues, including breast, ovarian, cervical, colorectal, renal, and nasopharyngeal tumours, but is expressed to a very limited extent in normal tissues (Turk H. et al., 2002; Wu J. et al., 2006). The folic acid receptor is also expressed in activated macrophages that persist in sites of inflammation, in inflammatory diseases such as Rheumatoid Arthritis (RA) (Chen W. et al., 2005; Paulos C. et al., 2004). The use of folic acid as a basis to obtain conjugates to transport exogenous compounds across cell membranes can a targeted delivery approach to the treatment and diagnosis of disease (ex., cancer and RA) and can provide a reduction in the required dose of therapeutic compounds. Furthermore, therapeutic bioavailability, pharmacodynamics, and pharmacokinetic parameters can be modulated through the use of bioconjugates, including folate bioconjugates. The use of folate ligands as a targeting device provides a number of important advantages over other targeting ligands. They are inexpensive, nontoxic, nonimmunogenic, easy to conjugate to carriers, retain high binding affinity, and are stable in storage and in circulation. (Shmeeda H. et al., 2006).

The use of folate conjugates to enhance transmembrane transport of exogenous molecules has been reported by Low et al., (EUA Pat. N° s 5.416.016, 5.108.921 and WO 90/12096). Manoharan et al. (International PCT publication N° WO 99/66063) describe certain folate conjugates and its synthesis method. The US 2006062842 patent (Gabizon et al., 2006) described a method of administering a compound encapsulated in liposomes as therapeutic to multi-drug resistant cancer cells. This method includes also the folic acid covalently bound to a hydrophobic polymer incorporated in liposomes. The same author (Gabizon at al, 2010) WO 2010143193, also describe the use of targeted liposomes by folic acid to enacapsulation of amino-biphosphate, to several diseases treatment. Sideratou al (2008), described in WO 2008010000 patent, modification of dendritic polymers with known groups, such as folic acid, with subsequent encapsulation in liposome bilayers, so-called preparing dendrionized liposomes. Dongkai et al. (2010), reported in CN 101684177 Patent the synthesis and use of folic acid conjugates linked to polyethylene glycol polycyanoacrylate (FA-PEG-PHDCA) due to excellent activity of the polymer and targeting property to cancer cells via folic acid, being the polymer applied to modify several vesicular systems such as liposomes. Although these studies reporting the use of folic acid as specific ligand to targeting, all formulations requires a prior binding of a polymer not specific to liposomal membranes. In the present invention, which describe peptide sequences with capacity of fixing in the liposomal membranes has the advantage of such formulations is not necessary to modification of liposomes with lipopolymers. The use of peptides to liposomes bonding have been explored based the so-called. "cell penetrating peptides". These peptides are capable of crossing cellular membranes in vitro and in vivo with high efficiency (Deshayes S. at al., 2005). Among them there are peptides derived from protein transduction domains, which are able to across biological membranes without transporter or receptor, and delivery peptides or molecules in intracellular compartments. Examples of such peptides include a Penetratin, TAT, Transportan and VP22 (Magzoub M. et al., 2001). There are also a number of amphipathic peptides which combine one hydrophobic domain with a hydrophilic domain. Among these ones it's possible to enumerate MAP, KALA, ppTG20, Trimer, P1, MPG, and Pep-1 (Morris, M. at al., 2008). Other peptides are further described as penetration capability due various characteristics. Thus, peptides with positive charge are used for translocation processes (Deshayes, S. et al., 2005). Despite the unique characteristics of these peptides identified above for binding to liposomes, have not been described as conjugated to specific ligands, which largely limits its use.

The present invention relates to peptide sequences which due to their hydrophobic sequence are capable of strong penetration/inclusion into liposomes. After a folic acid binding or antibody of folic acid receptor at the N-terminus, allows these liposomes possess the capability of targeting specific cells expressing the folic acid receptor. This enables the specific release of therapeutic agents and/or imaging agents that are inside the liposome, either hydrophobic or hydrophilic. The therapeutic agents may be either pharmaceutical compounds (active agents) or siRNA. These pharmaceutical formulations are capable of being administered either topically or by intravenous administration.

SUMMARY

The present invention relates to application of several peptide sequences conjugates into liposomes. The conjugation can be done with folic acid or with antibody of folic acid receptor, coupled to N-terminal peptide. The presence of these conjugated peptides in liposomal formulations allow the specific targeting and delivery of therapeutic agents and/or imaging agents in folic acid receptor over-expressed cells.

This method combines the ability of liposomes in the transport and release of drugs and specific expression of receptors at the cell membranes surface which allows transmembrane transport mediated by specific liposomes. Thus, allows transport of therapeutic agents and/or imaging agents that are inside the liposome, either hydrophobic or hydrophilic. Therapeutic agents may be either pharmaceutical compounds (active agents) or specific siRNA against defined target genes.

The present invention describe liposomes comprising a intra-liposomal core and a liposomal membrane and peptides of 10-22 amino acids having a sequence with a 95% degree of homology of the sequences selected from the following list. SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO 10, SEQ ID NO: 11, SEQ ID NO: 12 e SEQ ID NO: 13; preferably having a degree of homology of at least of 96%, 97%, 98%, 99% or 100%; and comprising in its sequence a ligand of folic acid or an antibody of folic acid receptor in the N terminal connected to said membrane; and a therapeutic agent imaging, in a preferred embodiment the therapeutic or imaging agent can be hydrophobic or hydrophilic, particularly siRNAs or a drug.

In a preferred embodiment the liposomes contains the peptide sequences described above, and whose liposomal membrane may contain phospholipids anionics, cationics or neutral in particular phosphatidylcholines, phosphatidylethanolamines, phosphatidyaglycerols or mixtures thereof.

In another preferred embodiment the liposomes described in the present invention can also contain:
- a steroid, preferably cholesterol or its derivative, in particular cholesteryl hemisuccinate—CHEMS, among others;
- an antioxidant, particularly Vitamin E,
- an invisibility agent, preferably polyethylene glycol—PEG—in particular a PEG having a molecular weight ranging from 2000-5000 Daltons or a ganglioside namely a brain tissue devivated monosialoganglioside (GM1);
- or mixtures thereof.

In a preferred embodiment the PEG may be linked to a phospholipid, namely DSPE-MPEG conjugate phospholipid.

In a preferred embodiment the liposomes described above may have a diameter ranging between 100-5000 nm, preferably 70-140, more preferably 120 nm.

Liposomes object of the present invention can be used in medicine, particularly in the treatment of inflammatory diseases, particularly rheumatoid arthritis, or for treatment of neoplasms in particular cancer.

The present invention further describes pharmaceutical compositions comprising liposomes containing the peptide sequences described above. Such compositions may be formulated for topical, oral, parenteral, injection, particularly L or intravenous, subcutaneous and intramuscular administration.

The present invention further describes a method of liposomal production which is the lipidic film hydration method, comprising dissolving a lipidic film in an aqueous buffer such as PBS—Phosphate Buffered Saline—containing peptides with a SEQ ID NO: 1-13.

Liposomes can be prepared by several known methods, namely by hydration of lipidic film method. Briefly, a known amount of one phospholipid (ex. EPC) to liposomal formation is dissolved in chloroform, and can further containing steroid (ex. cholesterol), and/or agent to increase invisibility (ex. DSPE-MPEG or GM1), and/or anti-oxidant (ex. Vitamin E) and a therapeutic compound or imaging agent (ex. Celecoxib drug), if this was hydrophobic. The organic solvent was evaporated under reduced pressure by using rotary evaporator to remove traces of the chloroform. The resulting dried lipid film was dispersed in aqueous PBS buffer, which containing Peptides comprising SEC ID NO: 1-13 as previously described and/or a pharmacological compound or imaging agent, if this was hydrophilic. The mixture was vortex mixed to yield liposomes.

DETAILED DESCRIPTION OF INVENTION

The present invention concerns in the application of several peptide sequences conjugates, which due to their hydrophobic sequence are capable of strong penetration into liposomes, in the lipid bilayer or liposomal membrane. The peptides attach to the liposomes in the hydrophobic layers—i.e. in the lipid bilayer or liposomal membrane—so that its conjugate (folic acid or antibody of folic acid receptor) are located on the surface of the liposome.

These liposomes combine the ability of liposomes in the transport and release of drugs and specific expression of receptors at the cell membranes surface which allows transmembrane transport mediated by specific liposomes. Thus, allows transport of therapeutic agents and/or imaging agents that are inside the aqueous core of liposome-liposomal nucleus, or in the lipid bilayer, either hydrophilic or hydrophobic, respectively. Therapeutic agents may be either pharmaceutical compounds (active agents) or specific siRNA against defined target genes.

Will be described several sequences of peptide conjugates that due to its hydrophobic sequence are capable of strong penetration into liposomes, which allow an improvement in the transmembrane transport The folic acid molecule which is binding to the N-terminus allows for specific liposomes targeting to cells expressing folate receptor. The peptides sequences based on the surfactant proteins sequence present in lung surfactant, the alveoli of mammalian lungs. The knowledge that surfactants proteins are able to recognize and interact with lipids lead to the assumption that fragments or models representing these proteins could interact with the phospholipid bilayer of the liposomes. This ability to interact with lipids, coupled with the fact that they are based on endogenous proteins make these peptide conjugates have great interest in the application of liposomes for use in the pharmaceutical field.

The peptides obtained by chemical synthesis, that bind, to liposomal bilayer may be selected from the following list (written the N-terminus (left) to the C-terminus (right)):

SEQ ID NO: 1: ácido fólico—KRFFPDTEGIKELD
SEQ ID NO: 2: ácido fólico—KRILPDTLGIKLLD
SEQ ID NO: 3: ácido fólico—ILLRKLMVPFFIRIGFRGRPAAS
SEQ ID NO: 4: ácido fólico—ILLRKLHVPIIPIGIRGRPAAS
SEQ ID NO: 5: ácido fólico—ILLRKLHVPWWPIGWRGRTAAS
SEQ ID NO: 6: ácido fólico—ILLRELHVPYYPIGYRGRPAAS
SEQ ID NO: 7: ácido fólico—ILLRKIHVAHGAIGIRGRPAAS
SEQ ID NO: 8: ácido fólico—ILLRKLHVCHGCIGIRGRPAAS
SEQ ID NO: 9: ácido fólico—DRDDQGQVQHL
SEQ ID NO: 10: ácido fólico—DRDDQAAFSQY
SEQ ID NO: 11: ácido fólico—DRDDGAGAGAGAGAGAGAGA
SEQ ID NO: 12: ácido fólico—DRDDVQHLQAAF
SEQ ID NO: 13: ácido fólico—DRDDILQTAGAL and comprising in their sequence a folic acid or an antibody of folic acid receptor in the N terminal binding to said membrane.

A variety of phospholipids that can be used in the liposomes formation, allows that a wide range of therapeutic agents and/or image for different pharmaceutical applications could be encapsulated, to different pharmaceutical applications.

Liposomes are prepared by the thin film hydration method. An amount of phospholipids, which can be anionic, neutral or cationic, is dissolved in chloroform and then the organic solvent is evaporated on a rotary evaporated. Unmodified liposomes (liposomes without PEG or GM1) do not survive long in circulation, as they are removed by macrophages. One of the first attempts to overcome these problems was focused on the manipulation of lipid membrane components in order to modify bilayer fluidity, as example by inclusion of a steroid. In this way, our liposomal formulations may preferentially containing cholesterol (CH), which may vary from molar ratio of 35-55%, preferably 38-40%. It was demonstrated that incorporation of cholesterol, into liposomes reduces interaction with blood proteins, by causing increased packing of phospholipids in the lipid bilayer. Cholesterol-free liposomes have also been shown to aggregate rapidly in the absence of steric stabilization and it is observed that this size instability also leads to increased clearance and decreased storage stability.

We used Egg phosphatidylcholine (EPC), which is a mixture of molecular species of PC differing in fatty acyl chains, and it includes a considerable amount of unsaturated fatty acids, such as arachidonic (C20:4) and decasohexanoic (C22: 6) acids. However, these phopholipids with unsaturated acyl chains are subject to oxidation, which may affect the permeability of the bilayers and the in vivo performance of the liposomes. In another preferential execution, can be used an anti-oxidant, for example Vitamin E ($\alpha$-tocopherol), which allow that lipid peroxidation products were virtually nonsignificant. The addition of $\alpha$-tocopherol in the formulation inhibits peroxidation of liposomes preventing free radical generation. To overcome the peroxidation of liposomes, the liposomes may containing an anti-oxidant agent, preferentially Vitamin E, in an amount, which can vary between 2-20 µM, preferably 8 µM.

Despite certain technical advantages, at least one obstacle currently impedes the widespread implementation of liposomes as drug carriers in vivo. Because unmodified liposomes do not survive long in circulation, but instead are removed by macrophages of the reticuloendothelial system within a few hours of administration, thus in a preferential execution was include a synthetic polymer, polyethyleneglycol (PEG) to the liposomes. PEG can be incorporated in the liposome surface by several ways, being the binding of polymer at membrane surface by crosslinking with a lipid (for example, PEG—distearoylphosphatidylethanolamine [DSPE]), the most used method actually. This has extended the blood circulation of conventional liposomes to drug delivery, the conjugated phospholipid DSPE-MPEG was incorporated in lipidic film of these new formulations, in a molar ratio which may vary between 4-12%, preferably 5-10%.

PEG-containing liposomes showed less binding to blood proteins, reduced RES uptake, and thus prolonged duration of liposomes in the circulatory system. Prolonged circulation of liposomal drugs could reduce the toxicity of drugs by changing their biodistribution. Furthermore, prolonged circulation provided the opportunity to access target sites by enhancing access to the pathological tissues and target cells from the vascular compartment. The results obtained demonstrated that despite the liposomes prepared with a 4-12% molar ratio of PEG, preferentially a 4-12% molar ratio of PEG and a peptide linked to folic acid show a high specificity for cancer cells that express the folate receptor. The liposomes prepared with 5% of PEG still have a low specificity for activated macrophages, which express the folate receptor $\beta$ (ex. disease: rheumatoid arthritis). In this way, were prepared liposomes with 10% of PEG. This increase of PEG concentration may increase the stealth degree of liposomes and promote specificity degree of folic acid targeting to activated macrophages.

Furthermore, it has been demonstrated that surface-modified liposomes with gangliosides have a prolonged circulation time in the blood stream compared to non-modified ones. These characteristics are potentially useful for applications of gangliosides in immunotherapies. Several glycolipids have been tested in studies of RES uptake of liposomes after intravenous injection: the glycolipid GM1 (a brain-tissue-derived monosialoganglioside) significantly decreased RES uptake when incorporated on the liposome surface, and the formulation remained in blood circulation for several hours. The degree of macrophage uptake depends on the concentration of GM1 in liposomes: a concentration of 10 mol % decreased RES uptake by 90%. GM1 were used as alternative to pegylated liposomes. In this way, the concentration of PEG or GM1 should be at least 5%, preferably at least 10% molar ratio.

TABLE I

Cell internalized different liposomal formulations (%).

| Phospholipid | Steroid | Agent increase invisibility | Targeting ligand peptide | Caco-2 (cancer cell line) | Activated Macrophages |
|---|---|---|---|---|---|
| EPC 57% | Cholesterol 38% | PEG 5% | Folate-peptide 0% | 10 | 89 |
| EPC 57% | Cholesterol 38% | PEG 5% | Folate-peptide 0.3% | 80 | 94 |
| EPC 57% | Cholesterol 38% | PEG 5% | Folate-peptide 0.75% | Not done | 95 |
| EPC 52% | Cholesterol 38% | PEG 10% | Folate-peptide 0% | Not done | 27 |
| EPC 52% | Cholesterol 38% | PEG 10% | Folate-peptide 0.3% | Not done | 65 |
| EPC 52% | Cholesterol 38% | PEG 10% | Folate-peptide 0.75% | Not done | 85 |
| EPC 52% | Cholesterol 38% | GM1 10% | Folate-peptide 0% | Not done | 35 |
| EPC 52% | Cholesterol 38% | GM1 10% | Folate-peptide 0.75% | Not done | 75 |

The resulting dried lipid film was dispersed in PBS (Phosphate Buffered Saline) buffer, which containing the peptides described of SEQ N° 1 to 13. This mixture was vortexed to yield multilamellar vesicles, which were then extruded to form unilamellar vesicles. Subsequently not incorporated compounds are separated by passage on a gel filtration column.

The presence of folic acid at the surface of liposomes prepared with peptides is determined and quantified using the RIDASCREEN®FAST kit. The basis of the test is antigen-antibody reaction where antibody free bind the enzyme peroxidase labeled folic acid which converts the chromogen into a quantifiable blue product.

The cellular uptake of the liposomes prepared with peptide was assessed by confocal microscopy, comparing internalization in folate receptor positive and negative cells. This analysis is possible due the presence of Oregon green 488 dye covalently bound at the peptide C-terminal. In the condition of the same exciting laser wavelength, it was shown a higher internalization of liposomes in over-expressed folate receptor cells (MDA-MB-468), because the cytoplasm seems to be much brighter in folic acid receptor positive cells than in negative cells (MDA-MB-435).

Taking into account these results, we quantified by fluorescence the cellular uptake of liposomes in these two types of cells. Quantification of cellular fluorescent peptide content was performed using a fluorescence spectrophotometer after cellular lysis and solubilisation of the cellular content. The results obtained showed that liposomes are preferentially internalized into cells with folate receptor, suggesting a specific internalization mediated by folic acid receptor.

In order to characterize peptide-liposome interaction to discriminate between a deep insertion of the peptide in the bilayer and poor adsorption of the peptide at the membrane surface, a tryptophan (Trp) residue was include in C-terminal side of the peptidic sequences. One blue shift in the fluorescence emission maximum and changes in quantum yield are observed when tryptophan is transferred from a polar medium to a less polar environment, which can be used to study the binding of peptides to lipid membranes (Zhao H. & Kinnunen P., 2002). In aqueous medium, the emission has its maximum at ≈360 run, indicating that the Trp residues are fully exposed to the water solvent. The results demonstrated that all peptides penetrate into liposomes.

Some peptides change their secondary structure upon interaction with the lipid bilayer. We employed Circular Dichroism (CD) spectroscopy to monitor the peptide secondary structure both in buffer solution and in the presence of liposomes. CD spectra revealed a predominant α-helix secondary structure component for peptides in aqueous buffer. Alteration of secondary structure of different peptides in contact with liposomes evident by the alteration of peptides CD spectra, demonstrating that peptides interact in liposomes.

These formulations can be administrated by intravenous or topic level.

Preferential Executions

To easier understanding the invention is included a preferred embodiments, which should not be regarded as limiting.

Obtaining liposomes bound peptide conjugate to folic acid containing an anti-inflammatory drug (celecoxib), for intravenous application in anti-inflammatory diseases, with peptides comprising at least one of following sequences SEQ ID NO: 9 a SEQ ID NO: 13.

Materials
EPC—Egg phosphatidylcholine
CH—Cholesterol
DSPE-MPEG—[N-(carbonyl-methoxypolyethylene glycol-2000)-1,2-distearoyl-sn-glycero-3-phosphoethanolamine]
Folic acid-Peptide
Vitamin E
Celecoxib Method Liposomes were prepared with the following composition: EPC/CH/MPEG-DSPE/Peptide-Folic acid with SEQ ID NO: 10-(57:38:4.7:0.3) 3 mM, Vitamin E 8 μM. The anti-inflammatory drug celecoxib was incorporated in the liposomes, in the molar ratio 5:1 (EPC:drug), corresponding to 65 μM, by dissolving in chloroform, during the formation of the lipid film. Subsequently, the lipid film was hydrated with PBS buffer containing the Folic acid-peptide. The multilamellar vesicles formed were subjected to extrusion by 7 passages with a 200 nm filter, followed by 12 passes through the 100 nm filter (Lipex Biomembranes, Vancouver, BC). Not incorporated compounds were removed by passing through a gel filtration column. The liposomes were sterilized by filtration through a 0.22 μm filter and stored at 4° C.

After obtaining the above liposomes, these were subjected to an exhaustive physicochemical characterization. The size distribution was obtained by the photon correlation spectroscopy technique in the Zeta Sizer NS equipment, liposomes having a diameter of approximately 120 nm and a monodisperse population. The surface charge of these liposomes was measured as zeta potential obtained in Zeta Sizer NS, presenting approximately neutral charge. These liposomes were also analyzed by scanning electron microscopy in order to determine the morphology, presenting a spherical shape. This formulation was further characterized by mass spectroscopy, and the spectra can be observed that liposomes encapsulate celecoxib. These liposomes showed great stability over four months. Cytotoxicity assays revealed that liposomes empty and with the drug did not exhibit cytotoxicity on human cell lines "normal" (human fibroblast-BJ5ta). The liposomes with the drug present increased toxicity in expressed folate receptor cancer cell lines than compared with empty liposomes. This result is in agreement with the fact that the liposomes containing the drug have demonstrated ability to be internalized more efficiently by folate receptor cancer cells than in the cancer cell without expression of folic acid receptors. Such as celecoxib is a specific cyclogenase inhibitor, we proceed to determine the effect of the drug by quantifying the expression of this gene, by Real-time PCR. The results confirm the decreased expression of COX-2 in cancer cells Caco-2, a cell line with expression of folate receptor, after incubation with liposomes containing celecoxib.

TABLE II

Effect of different liposomal formulation with and without Folate-peptide and celecoxib in COX-2 mRNA expression in Caco-2 cells (values of relative expression).

| Treatment | Relative expression |
|---|---|
| (—) | 1.00 |
| Liposomes | 0.87 |
| Liposomes – Folate-peptide SEQ ID NO: 10 DRDDQAAFSQY | 0.47 |
| Liposomes + Celecoxib (65 µM) | 0.49 |
| Liposomes – Folate-peptide SEQ ID NO: 10 DRDDQAAFSQY + Celecoxib (65 µM) | 0.20 |
| Celecoxib (65 µM) | 0.14 |

Amino Acids List
A—Alanine
C—Cysteine
D—Aspartic acid
E—Glutamic acid.
F—Phenylalanine
G—Glycina
H—Histidine
I—isoleucine
K—Lysine
L—Leucine
M—Methionine
N—Asparagine
P—Praline
Q Glutamine
R—Arginine
S—Serine
T—Threonine
V—Valine
W—Tryptophan
Y—Tyrosine

REFERENCES

Chen, Tonggian (Irvine, Calif., US), Haeberli, Peter (San Francisco, Calif., US), Vargeese, Chandra (Schwenksville, Pa., US), Wang, Weimin (Churchville, Pa., US), (2011). Conjugates and Compositions for Cellular Delivery. United States Chen W. Mahmood U., Weissleder R. & Tung C. (2005). Arthritis imaging using a near-infrared fluorescence folate-targeted probe. Arthritis Res Ther, 7:R310-R317

Chrai S., Murari R. & Ahmad I. (2002). Liposomes (a Review). Part Two: Drug Delivery Systems. BioPharm, 40-49

Constantinos, Paleos (GR), Oreozili, Sideratou (GR), Dimitrios, Tsiourvas (GR), Theodosios, Theodosiou (GR), (2008). Molecular Dendritic Transporters. National Center for Scientific Research.

Deshayes S., Morris M., Divita G. & Heitz F. (2005). Cell-penetrating peptides: tools for intracellular delivery of therapeutics. Cell. Mol. Life Sci., 62: 1839-1849

Drummond D., Noble C., Hayes M., Park J. & Kirpotin D. (2008). Pharmacokinetics and in Vivo Drug Release Rates in Liposomal Nanocarrier Development. J Pharm Sci, 97: 4696-4740

Errico G., Vitiello G., Ursi A. & Marsh D. (2009). Interaction of short modifed peptides deriving from glycoprotein gp36 of feline immunodefciency virus with phospholipid membranes. Eur Biophys J., 38:873-882

Gabizon A., Horowitz A., Goren D., Tzemach D., Mandelbaum-Shavit F., Qazen M. & Zalipsky S. (1999). Targeting Folate Recetor with Folate Linked to Extremities of Poly (ethylene glycol)-Grafted Liposomes: In Vitro Studies. Bioconjugate Chem., 10: 289-298

Gabizon, Alberto A. (Jerusalem, Ill.), Zalipsky, Samuel (Redwood City, Calif., US), Goren-rubel, Dorit (Jerusalem, Ill.), Horowitz, Aviva T. (Jerusalem, Ill.), (2006). Method of administering a compound to multi-drug resistant cells. United States. Alza Corporation, Hadasit Medical Research and Development Ltd.

Haagsman H & Diemel R. (2001). Surfactant-associated proteins: functions and structural variation, Comparative Biochemistry and Physiology—Part A: Molecular & amp; Integrative Physiology, 129: 91-108

Hong M., Lim S., Lee M., Kim Y. & Kim C. (2001). Prolonged Blood Circulation of Methotrexate by Modulation of Liposomal Composition. Drug Delivery, 1(8): 231-237

Huang Y., Chung T. & wu C. (1998). Effect of saturated: unsaturated phosphatidylcholine ratio on the stability of liposome-encapsulated haemoglobin. International Journal of Pharmaceutics, 172: 161-167

Immordino M., Dosio F. & Cattel L. (2006). Stealth liposomes: review of the basic science, rationale, and clinical applications, existing and potential. International Journal of Nanomedicine, 1(3): 297-315

Lang J., Vigo-Pelfrey C. & Martin F. (1990). Liposomes composed of partially hydrogenated egg phosphatidylcholines: fatty acid composition, thermal phase behavior and oxidative stability. Chemistry and Physics of Lipids, 53(1): 91-101

Lee R. & Low P. (1994). Delivery of Liposomes into CulturedK B Cells via Folate Recetor-mediated Endocytosis. The Journal of Biological Chemistry, 269(4): 3198-3204

Low, Philip S. (West Lafayette, Ind.), Horn, Mark A. (West Lafayette, Ind.), Heinstein, Peter F. (West Lafayette, Ind.) (1995). Method for enhancing transmembrane transport of exogenous molecules. United States, Purdue Research Foundation (West Lafayette, Ind.)

Magzoub M., Kilk K., Eriksson L., Langel U. & Graslund A. (2001). Interaction and structure induction of cell-penetrating peptides in the presence of phospholipid vesicles. Biochimica et Biophysica Acta, 1512: 77-89.

Morris M., Deshayes S., Heitz F. & Divita G. (2008). Cell-penetrating peptides: from molecular mechanisms to therapeutics. Biol. Cell, 100: 201-217

Paulos C., Turk M., Breur G., & Low P. (2004). Folate receptor-mediated targeting of therapeutic and imaging agents to activated macrophages in rheumatoid arthritis Advanced Drug Delivery Reviews 56: 1205-1217

Shmeeda, Hilary (IL), Gabizon, Alberto A. (Jerusalem, Ill.), (2010). Targeted liposomes comprising N-containing biphosphonates and uses thereof. Yissum Research development Company of the Hebrew University of Jerulalem, LTD Shmeeda H., Mark L., Tzemach D., Astrahan P., Tarshish M. & Gabizon A. (2006). Intracellular uptake and intracavitary targeting of folateconjugated liposomes in a mouse lymphoma model with up-regulated folate receptors. Mol Cancer Ther, 5(4): 818-824

Turk M., Breur G., Widmer W., Paulos C., Xu L., Grote L & Low P. (2002). Folate-Targeted Imaging of Activated Macrophages in Rats With Adjuvant-Induced Arthritis. Arthritis & Rheumatism, 46(7): 1947-1955

Varghese B. Haase N & Low P. (2007). Depletion of Folate-Recetor-Positive Macrophages Leads to Alleviation of Symptoms and Prolonged Survival in Two Murine Models of Systemic Lupus Erythematosus. Molecular Pharmaceutics, 4: 679-685

Wang, Dongkai, Li, Xiang, Pan, Weisan, Qiu, Lipeng, (2010). Folate-conjugated polyethylene glycol polyalkylcyanoacrylate, preparation method and application thereof. Univ Shenyang Pharmaceutical Wu J., Liu Q. & Lee R. (2006). A folate receptor-targeted liposomal formulation for paclitaxel. International Journal of Pharmaceutics, 316: 148-153

Zhao H & Kinnunen P. (2002). Binding of the Antimicrobial Peptide Temporin L to Liposomes Assessed by Trp Fluorescence. The Journal of Bioioglcal Chemistry, 277: 25170-25177

The present invention is in any way restricted to the executions described herein and a person with average knowledge of the area may provide many possibilities for modifications thereof without departing from the general idea of the invention as defined in the claims.

The preferred embodiments described above are obviously combinable. The following claims define further preferred embodiments of the present invention.

The invention claimed is:

1. A preparation comprising liposomes wherein the liposomes comprise an intra-liposomal core and a liposomal membrane, one or more peptides each of which is 10-22 amino acids in length and has a sequence that is at least 95% homologous to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, wherein the peptide comprises a folic acid ligand or an antibody of a folic acid receptor and is bound at its N-terminus to the liposomal membrane; and a therapeutic or imaging agent.

2. The preparation of claim 1, wherein the liposomes comprise phospholipids which are anionic, neutral or cationic.

3. The preparation of claim 1, wherein the liposomes further comprise at least one of the following: a steroid, an anti-oxidant, an agent of invisibility or a mixture thereof.

4. The preparation of claim 3, wherein the steroid is cholesterol or cholesteryl hemisuccinate (CHEMS).

5. The preparation of claim 3, wherein the anti-oxidant is vitamin E.

6. The preparation of claim 3, wherein the agent of invisibility comprises a polyethylene glycol (PEG) or a ganglioside.

7. The preparation of claim 6, wherein the ganglioside is a brain tissue derived monosialoganglioside (GM1).

8. The preparation of claim 6, wherein the polyethylene glycol (PEG) is bound to a phospholipid.

9. The preparation of claim 8, wherein the molecular weight of the PEG is between 2000 and 5000 Daltons.

10. The preparation of claim 1, wherein the therapeutic or imaging agent is hydrophobic or hydrophilic.

11. The preparation of claim 10, wherein the therapeutic agent is a siRNA or a pharmaceutical compound.

12. The preparation of claim 11, wherein the liposomes have a diameter between 100 and 5000 nm.

13. The preparation of claim 1, adapted for use in a medical application.

14. The preparation of claim 13, wherein the medical application is treatment of an inflammatory disease or a neoplasia.

15. A pharmaceutical composition comprising the preparation of claim 1.

16. The pharmaceutical composition of claim 15 formulated for topical, oral, parenteral, injectable, intravenous, subcutaneous or intramuscular administration.

17. A method of producing the preparation of claim 1, wherein the lipidic film is hydrated with an aqueous buffer which contains one or more peptides each of which is 10-22 amino acids in length and has a sequence at least 95% homologous to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

18. The preparation of claim 2, wherein the liposomes further comprise at least one of the following: a steroid, an anti-oxidant, an agent of invisibility or a mixture thereof.

19. The preparation of claim 7, wherein the polyethylene glycol (PEG) is bound to a phospholipid.

20. The preparation of claim 11, wherein the liposomes have a diameter between 70 and 140 nm.

* * * * *